United States Patent [19]

Munoz

[11] Patent Number: 5,792,180

[45] Date of Patent: Aug. 11, 1998

[54] HIGH BEND STRENGTH SURGICAL NEEDLES AND SURGICAL INCISION MEMBERS AND METHODS OF PRODUCING SAME BY DOUBLE SIDED PHOTOETCHING

[75] Inventor: Marcelino P. Munoz, Waterbury, Conn.

[73] Assignee: United States Surgical Corporation, Norwalk, Conn.

[21] Appl. No.: 590,256

[22] Filed: Jan. 23, 1996

[51] Int. Cl.$^6$ .................................................. A61B 17/06
[52] U.S. Cl. ........................................ 606/223; 430/320
[58] Field of Search ..................................... 430/320, 317, 430/313, 323; 606/222, 223

[56] References Cited

U.S. PATENT DOCUMENTS

| | | |
|---|---|---|
| 2,242,967 | 5/1941 | Carlile . |
| 2,326,022 | 8/1943 | Everett . |
| 2,469,689 | 5/1949 | Gresham . |
| 2,479,464 | 8/1949 | Bliss . |
| 2,735,763 | 2/1956 | Heath . |
| 3,038,475 | 6/1962 | Orcutt . |
| 3,054,172 | 9/1962 | Turney, Jr. . |
| 3,162,871 | 12/1964 | Powers . |
| 3,348,669 | 10/1967 | Powers . |
| 3,358,363 | 12/1967 | Jacks et al. . |
| 3,551,227 | 12/1970 | Burgess . |
| 3,808,001 | 4/1974 | Konstantouros et al. . |
| 3,816,273 | 6/1974 | Synder . |
| 3,822,461 | 7/1974 | Malmstrom . |
| 3,942,981 | 3/1976 | Sato . |
| 4,080,709 | 3/1978 | Poler . |
| 4,215,194 | 7/1980 | Shepherd . |
| 4,282,311 | 8/1981 | Dinardo, Jr. . |
| 4,587,202 | 5/1986 | Borysko . |
| 4,672,734 | 6/1987 | Kawada et al. . |
| 4,711,800 | 12/1987 | DiVincenzo . |
| 4,777,096 | 10/1988 | Borysko . |
| 4,785,868 | 11/1988 | Koenig, Jr. . |
| 4,793,218 | 12/1988 | Jordan et al. . |
| 4,842,969 | 6/1989 | Kawatsuki et al. . |
| 4,890,614 | 1/1990 | Kawada et al. . |
| 4,960,659 | 10/1990 | Sagou ........................................ 430/323 |
| 5,001,323 | 3/1991 | Matsutani et al. . |
| 5,057,401 | 10/1991 | Borysko et al. . |
| 5,178,628 | 1/1993 | Otsuka et al. . |
| 5,330,441 | 7/1994 | Prasad et al. . |
| 5,403,344 | 4/1995 | Allen . |
| 5,411,613 | 5/1995 | Rizk et al. . |
| 5,478,344 | 12/1995 | Stone et al. . |

FOREIGN PATENT DOCUMENTS

| | | |
|---|---|---|
| 24 05 998 A1 | 2/1974 | Germany . |
| 27 37 648 A1 | 8/1977 | Germany . |
| 34 14 262 A1 | 4/1984 | Germany . |

*Primary Examiner*—Michael Buiz
*Assistant Examiner*—William W. Lewis

[57] ABSTRACT

There is provided a high bend strength double pointed surgical needle, or surgical incision member, which includes a suture hole intermediate the points and a pair of crimping bulges adjacent the suture hole. The high strength surgical needle further includes transverse slots adjacent each pointed end. There is also disclosed a method of forming a plurality of high bend strength surgical needles from a sheet of needle stock including coating both sides of the sheet of needle stock with a photoresist, exposing both sides of the sheet of needle stock to light in the image of a plurality of surgical needle blanks connected at either pointed end to carrier strips, subjecting the sheet so exposed to an etchant to remove all unexposed metal and removing the surgical needle blanks from the sheet

11 Claims, 5 Drawing Sheets

HIGH BEND STRENGTH SURGICAL NEEDLES AND SURGICAL INCISION MEMBERS AND METHODS OF PRODUCING SAME BY DOUBLE SIDED PHOTOETCHING

BACKGROUND

1. Technical Field

This disclosure relates generally to surgical needles, and surgical incision members used in conjunction with endoscopic or laparoscopic suturing apparatus, and, more particularly, to high bend strength surgical needles and methods of producing same by double sided photoetching of needle stock.

2. Description of Related Art

The production of surgical needles from needle stock is often a complex process. As used herein the terms "surgical needle blanks" and "surgical incision member blanks" refer to a piece of needle stock material at various stages of completion but not fully formed into a surgical grade needle or incision member suitable for use during surgical procedures. Various types of methods have been developed to form surgical needle blanks and needles. These methods include metal working the needle stock by cutting, stamping, pressing or bending the needle stock to impart the desired characteristics to the needle blanks or by other methods such as grinding to remove material from the needle stock. Often these methods introduce stresses into the needle blanks which may tend to weaken the needle blanks slightly. The strength of a finished surgical needle is particularly important where the surgical needle may be subject to bending forces during use, which forces, if high enough, may permanently deform the surgical needle. The bend strength of needles can be tested by measuring the bend moment or the degree of deflection of the needles when subject to predetermined loads and bend or rotational distances, without suffering permanent deformation.

Certain complex surgical needles may require several operations to fully form the needles. One such type of needle, a surgical incision member disclosed in U.S. patent application Ser. No. 08/260,759, filed Jun. 16, 1994, and entitled SURGICAL INCISION MEMBERS, the disclosure of which is incorporated by reference herein, is a double pointed surgical needle having suture attachment structure intermediate the points. Preferably, the suture attachment structure is a suture hole with crimping bulges formed on opposed sides of the suture hole. Additionally, the surgical incision member may include apparatus engagement structure in the form of slots adjacent each pointed end which cooperate with a suitable surgical suturing apparatus such as that disclosed in U.S. patent application Ser. No. 08/293,233, filed Aug. 19, 1994, entitled SURGICAL SUTURING APPARATUS WITH LOADING MECHANISM. At each stage of formation of a complex surgical needle, such as the aforementioned surgical incision member, there is a chance that stresses may be induced into the needle blank either mechanically by stamping, cutting, etc., or thermally by grinding or even laser drilling or cutting of the needle blank.

Often the stresses introduced into the needle blanks are insufficient to weaken the needle blank enough to cause difficulties with the finished surgical needle during use. When used in sutuing tough tissues, however, it may be desirable to have an extra margin of strength designed into the needle to prevent bending of the needle during use. One way this may be accomplished is by increasing the dimensions of certain areas of the needle, particularly the center section of the needle body. However, the formation of such needles may still lead to mechanically and/or thermally induced stresses in certain critical areas of the needles. One method of forming surgical needles generally, and without mechanical operations, is by a process known as photoetching, such as that disclosed generally in U.S. Pat. Nos. 4,587,202; 4,777,096; and 5,057,401. These processes generally include coating a sheet of needle stock with a light sensitive and etchant resistant chemical, or photoresist, and exposing the coated sheet to light images in the form of needle blanks. The exposed photoresist hardens in the shape of the images and the unexposed photoresist is removed. The sheet is then subjected to an etchant which removes all the exposed metal of the sheet leaving only the needle blanks in the shape of the images. While the above described process is known, it is typically used only for relatively simple needle structures having a single pointed end. Upon breaking the needle blanks free of the stock material suture attachment structure may be formed at the end of the needle opposite the tip, such as by mechanical or laser drilling a hole or mechanical channeling, which may introduce stresses.

SUMMARY

A method is disclosed for simultaneously forming a plurality of high strength surgical needles, such as surgical incision members, from needle stock. The method generally includes coating both sides of a sheet of needle stock with a photoresist The coated sheet is then exposed on a first side to light in the image of a plurality of double pointed surgical needle blanks connected to one or more carrier strips at at least one pointed end. Preferably, the image additionally includes suture attachment structure in the form of a suture hole intermediate the points and crimping bulges extending outwardly from the body portion of the needle blank adjacent the suture hole area. Additionally, apparatus engagement structure in the form of transverse slots adjacent either pointed end may also be provided in the image. A second side of the coated sheet is also exposed to light in the image of a plurality of surgical needle blanks, which images preferably are in register with the images on the first side of the sheet. The images on the second side of the sheet may include all or just some of the features of the images on the first side of the sheet. Once the sheet has been exposed on both sides to light in order to harden the photoresist into images of a plurality of surgical needle blanks connected at each pointed end to carrier strips, the sheet is dried by baking at suitable temperatures which further serves to harden the exposed photoresist. The sheet is then subjected to a developer which removes the unexposed photoresist. The sheet, coated with the images of a plurality of surgical needle blanks connected by carrier strips, is then subjected to an etch bath which removes all of the uncoated needle stock. The result is a sheet containing a plurality of rows of double pointed surgical needle blanks connected at one or both pointed ends to the carrier strips. The sheet is then rinsed and may be heat treated to further strengthen the needle blanks. The surgical needle blanks are then either removed by mechanical means or by etching them free from the carrier strips. Preferably, once the needle blanks have been removed they are tumbled in a suitable tumbling media, for example, cut cylinders of aluminum oxide followed by tumbling in porcelain balls, to finish the pointed ends to a desired predetermined radius. Details of tumbling pointed needles to obtain the desired radius of curvature at the point of a needle are disclosed and claimed in U.S. patent application Ser. No. 08/325,847, filed Oct. 19, 1994, the disclosure of which is incorporated by reference herein. Also see U.S. Pat. No. 5,447,465.

3

There is also disclosed a sheet of surgical needle blanks including a plurality of double pointed surgical needle blanks connected at either pointed end to needle stock. Each needle blank includes suture attachment structure in the form of a suture hole intermediate the pointed ends and a pair of crimping bulges adjacent either side of the suture hole. Each needle blank further includes apparatus engagement structure in the form of transverse slots adjacent either pointed end.

There is also disclosed a high bend strength surgical needle. The surgical needle is a curved, double pointed needle having a suture hole intermediate the points and crimping bulges formed on either side of the suture hole. The surgical needle further includes transverse slots formed adjacent each pointed end. The surgical needle is preferably formed of Carpenter 455 series stainless steel such as that disclosed in U.S. Pat. No. 5,411,613.

BRIEF DESCRIPTION OF THE DRAWINGS

Various embodiments are described hereinbelow with reference to the drawings, wherein.

DETAILED DESCRIPTION OF PREFERRED EMBODIMENTS

Figure 1:
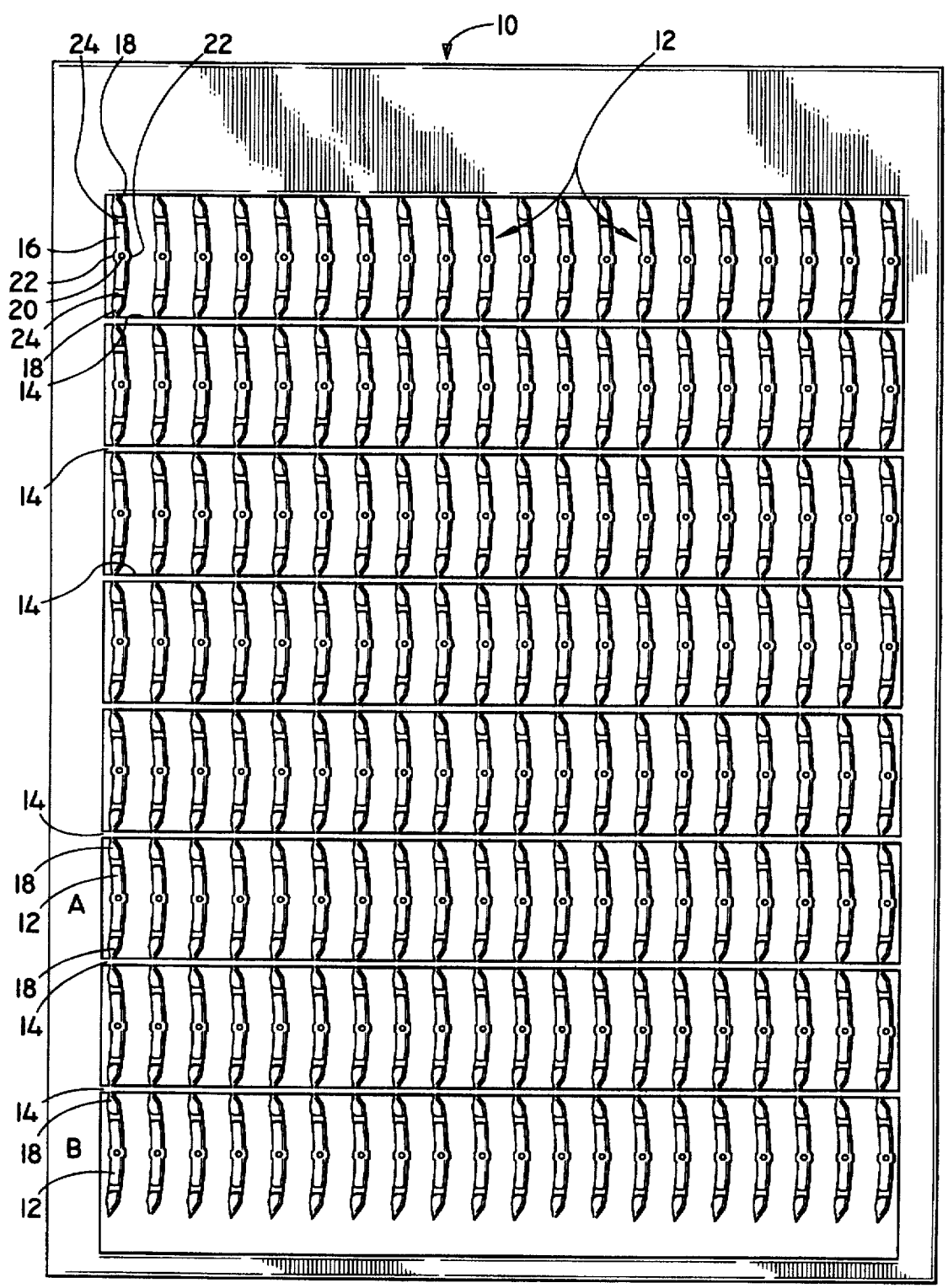
FIG. 1 is a plan view of a sheet of surgical incision member blanks formed according to the disclosed process.

Referring now to the drawings and initially to FIG. 1 there is shown a sheet 10 of high bend strength surgical incision member blanks, hereinafter "needle blanks" formed according to the disclosed method. Sheet 10 includes a plurality of rows of needle blanks 12 attached to parallel rows of carrier strips 14 extending across sheet 10. Needle blanks 12 may be attached to two carrier strips 14 as shown in row of needle blanks A or only to a single carrier strip 14 as shown in row of needle blanks B. Each needle blank 12 has a body portion 16 and a pair of opposed pointed end portions 18. When needle blanks 12 are attached to two carrier strips 14, as in row A, needle blanks 12 are preferably attached to carrier strips 14 at each pointed end portion 18. However, when needle blanks 12 are attached only to a single carrier strip 14, as in row B, needle blanks 12 are preferably attached to carrier strip 14 at only one of the pointed end portions 18. Preferably, body portion 16 of each needle blank 12 includes a suture hole 20 and a pair of opposed crimping bulges 22 extending outwardly of body portion 16 and adjacent suture hole 20. Body portions 16 may also include apparatus engagement structure, in the form of slots 24, formed in body portions 16.

Sheet 10 is generally formed from a sheet of suitable needle stock, such as, plastics, steels, composites, etc. The needle stock is coated on both sides with a suitable photoresist and exposed to light in the image of the needle blanks and carrier strips to harden the photoresist. The remaining unhardened photoresist is then removed and the coated needle stock is exposed to an etchant which removes all the uncoated needle stock. The result is sheet 10 including needle blanks 12 and carrier strips 14. During the etching process, the etchant "eats" substantially into the face of the unexposed needle stock, however, some lateral etching may also occur and may be compensated for, and even manipulated to beneficial use.

In order to expose the needle stock coated with photoresist to light in the image of the needle blanks and carrier strips, the light is shown through a negative image, or photomask, of the needle blanks and carrier strips. The photomask is typically made of glass for repeated use. By manipulating the characteristics of the photomask the characteristics of the resultant needle blanks and carrier strips may be controlled. When different characteristics are desired on opposed sides of the needles different masks may be used in exposing the photoresist on opposite sides of the needle stock to light.

Figure 2:
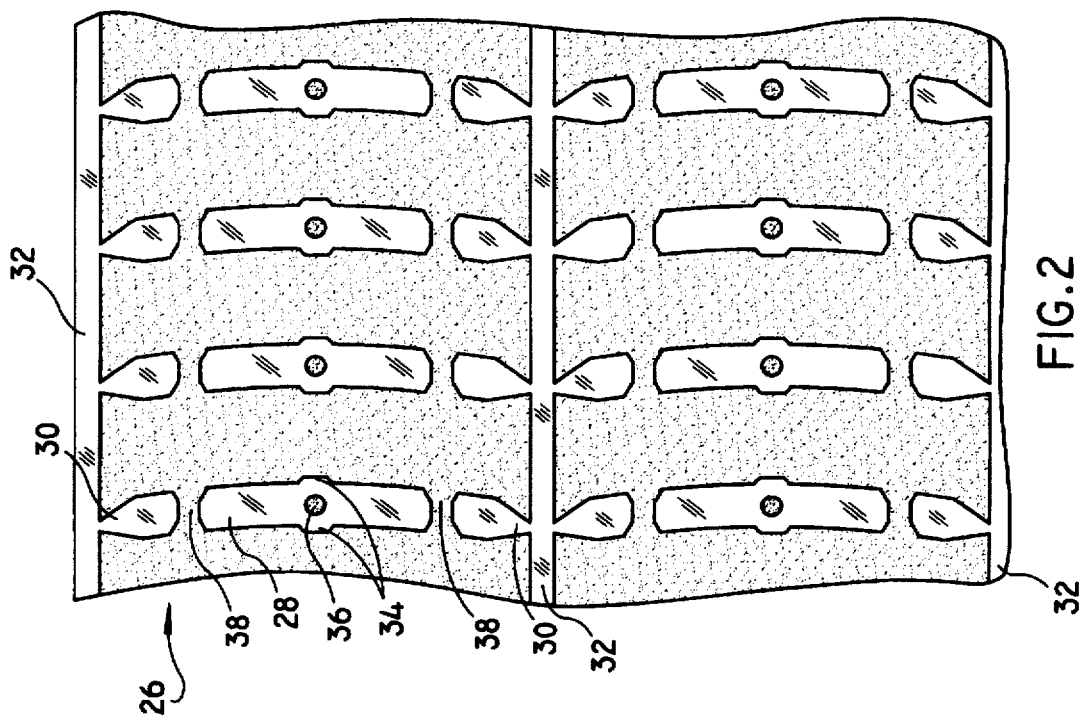
FIG. 2 is an enlarged partial plan view of one of the photomasks used in forming images on a first side of the sheet of surgical incision member blanks of FIG. 1.

Referring now to FIG. 2, a first photomask 26 includes both positive and negative image areas which correspond to needle stock to remain and be removed, respectively. Positive areas include body portion images 28 which correspond to body portion 16. Photomask 26 also includes pointed end images 30 and strip images 32 corresponding to pointed end portions 18 and carrier strips 14, respectively. As shown, pointed end images 30 and strip images 32 are connected so that the resultant needle blank 12 is connected to carrier strips 14 at both pointed ends 18. Obviously, where only one pointed end 18 and carrier strip 14 connection is desired, the photomask can be so modified. Photomask 26 may also include enlarged areas of body portion image 28, or bulge images 24, which correspond to crimping bulges 22.

In order to remove material from the metal sheet, certain areas of photomask 26 are left covered up, i.e., negative images. For example, in order to form suture hole 20 in needle blank 12, a suture hole image 36 is positioned intermediate bulge images 24. Similarly, slot images 28, corresponding to slots 24, are provided in photomask 26 adjacent pointed end images 30.

As noted above, different photomasks may be used on opposite sides of the needle stock where differing characteristics are desired on opposed sides of the needle blanks. Thus, where slots 24 are desired on only one side of the needle blanks, a second photomask without slot images 38 is used in exposing the opposing side of the needle stock to light.

Figure 3:
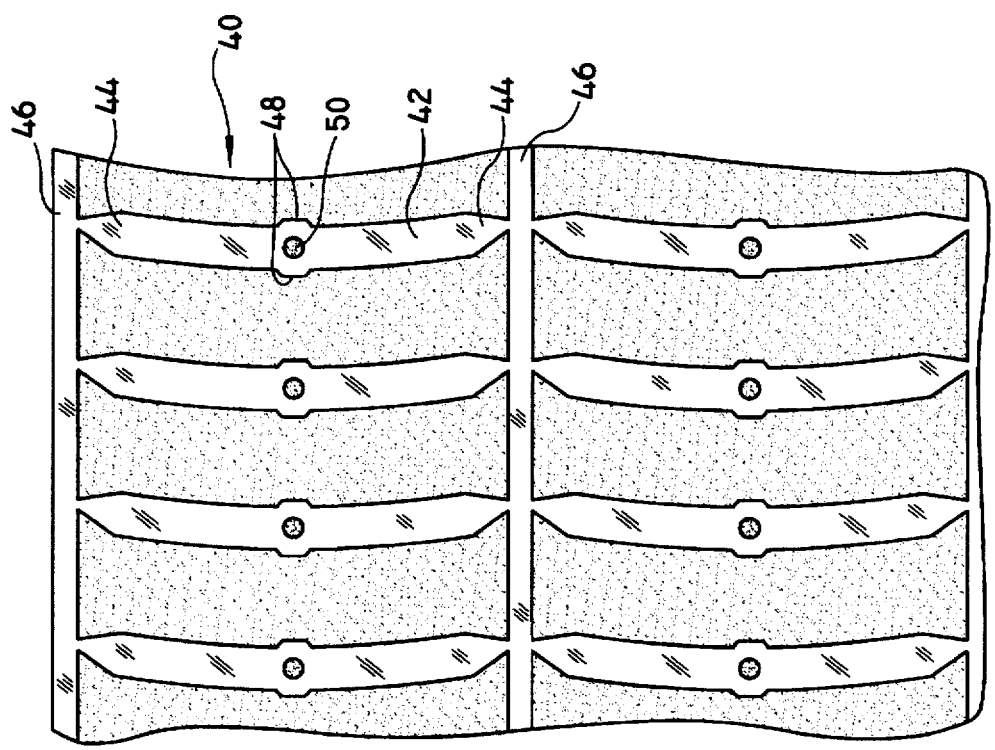
FIG. 3 is an enlarged partial plan view of a second photomask used in forming images on a second side of the sheet of surgical incision member blanks of FIG. 1.

Referring now to FIG. 3, a second photomask 40 is substantially identical to photomask 26 with the exception of the absence of slot images 38. Photomask 40 includes body portion images 42 and pointed end images 44 connected to strip images 46. Photomask 40 also includes bulge images 48 as well as a suture hole image 50. Photomask 40 is preferably dimensioned and configured to register exactly with photomask 26 in order to form uniform rows of needle blanks. For example, suture hole images 36 and 50 are lined up exactly opposite each other.

In order to form sheet 10 containing high strength surgical needle blanks 12 using the disclosed photomasks 26 and 40 a sheet of suitable strength metal is used, such as, for example, Carpenter 455 stainless steel disclosed in U.S. Pat. No. 5,411,613. The particular needle stock used is chosen based on its strength and use characteristics which, as described in more detail hereinbelow, may be increased by prior metal working and/or subsequent heat treating.

The general and specific compositions of preferred martensitic precipitation-hardening stainless steels are as shown on Table I:

invention is 1RK91™ steel, developed by A. B. Sandvik Steel, S-811 81 Sandviken, Sweden.

TABLE I

| | | | | | WEIGHT PERCENTS | | | | |
|---|---|---|---|---|---|---|---|---|---|
| ELEMENT | GENERAL COMPOSITION | PREFERRED COMPOSITION | CARPENTER 455 | STAINLESS W | 17-4 PH | 15-5 PH | PH 13 MO | CUSTOM 450 | SANDVIK 1RK91 |
| Fe | Balance | Balance | Balance | Balance | Balance | Balance | Balance | Balance | Balance |
| Cr | 10–17 | 11–13 | 11.0–12.5 | 16.5 | 16.0 | 15.0 | 12.5 | 15.0 | 11.7 |
| Ni | 4–11 | 7–10 | 7.5–9.5 | 6.75 | 4.0 | 4.0 | 8.0 | — | 9.1 |
| Ti | 0–1.6 | 0.8–1.4 | 0.8–1.4 | 0.8 | — | — | — | — | 1.0 |
| Mo | 0–6 | 0.5–4.5 | 0.50 | — | — | — | 2.5 | 1.0 | 4.1 |
| Cu | 0–4 | 1–3 | 1.5–2.5 | — | 3.2 | 4.0 | — | 0.75 | 2.0 |
| C | <0.02–0.07 | 0.015–0.06 | 0.05 | 0.07 | 0.04 | 0.07 | 0.05 | 0.05 | .004 |
| Mn | 0.5–0.6 | <0.5–0.6 | 0.50 | 0.5 | 0.25 | — | 0.5 | — | .17 |
| Si | <0.5–1 | <0.5–0.6 | 0.50 | 0.5 | 0.60 | — | 0.5 | 1.0 | .05 |
| P | 0–0.2 | 0–0.04 | 0.04 | — | — | 0.20 | — | — | — |
| S | 0–0.04 | 0–0.04 | 0.03 | — | 0.01 | — | — | — | .002 |
| Nb | 0–0.5 | 0–0.5 | 0.10–0.50 | — | — | — | — | 0.40 | — |
| Ta | — | — | — | — | — | — | — | — | — |
| Al | 0–1.1 | 0 | — | 0.4 | — | — | 1.1 | — | — |
| Nb + Ta | 0–0.6 | 0 | — | — | 0.25 | 0.35 | — | — | — |
| Cobalt | 0–6 | 0–3 | — | — | — | — | — | — | — |

Most preferably, the alloys contain a nickel-titanium ($Ni_3$-Ti) precipitation hardening phase. Preferably, such an alloy contains about 4 to about 11 weight percent nickel and about 0.0 to about 1.6 weight percent titanium, more preferably about 7 to about 10 weight percent nickel and about 0.8 to about 1.4 weight percent titanium.

A preferred alloy is 455 steel. This 455 stainless steel contains about 11 to about 12.5 weight percent chromium, about 7.5 to about 9.5 weight percent nickel, about 0.8 to about 1.4 weight percent titanium, about 0.5 to about 0.7 weight percent molybdenum, about 1.5 to about 2.5 weight percent copper, about 0.04 to about 0.06 weight percent carbon, about 0.4 to about 0.6 weight percent manganese, about 0.4 to about 0.6 weight percent silicon, up to about 0.04 weight percent phosphorus, about 0.02 to about 0.04 weight percent sulfur, about 0.1 to about 0.5 weight percent niobium, with iron as the remainder.

A class of precipitation hardenable alloys are disclosed by PCT Application WO 93/07303, incorporated herein by reference. This PCT application discloses a precipitation hardenable martensitic stainless steel alloy comprising, in percent by weight, about 10% to about 14% chromium, between about 7% to about 11% nickel, molybdenum between about 0.5% to about 6%, cobalt up to about 6%, copper between about 0.5% to about 4%, aluminum added up to about 0.6%, titanium between about 0.4% and about 1.4%, carbon and nitrogen not exceeding about 0.05%, with iron as the remainder and the content of any other element of the periodic table not exceeding about 0.5%. Preferably, the alloy has about 0.5% to about 3% copper, up to about 6% cobalt, and about 0.5% to about 4.5% molybdenum. More preferably, the alloy has up to about 3% cobalt. Most preferably, this stainless steel comprises about 11.5 to about 12.5 weight percent chromium, about 8.5 to about 9.5 weight percent nickel, about 0.8 to about 1.0 weight percent titanium, about 3.5 to about 4.5 weight percent molybdenum, about 0.5 to about 2.5 weight percent copper, up to about 0.02 weight percent carbon, up to about 0.5 weight percent manganese, up to about 0.5 weight percent silicon, up to about 0.02 weight percent sulfur, with the remainder consisting essentially of iron. A preferred martensitic precipitation-hardening alloy for use in the present Preferably, the sheet of metal has a thickness of approximately 0.030 to 0.040 inches.

The sheet of metal is coated on both sides with a chosen photoresistive material, such as KMER or RISTON, available from DuPont, using known methods. The coating is then dried by heating for a predetermined time at a low temperature.

Once the coating has dried, photomasks 26 and 40, either singly or simultaneously, are overlayed over the coated sheet in correct register. Various indicia may be provided on photomasks 26 and 40 to ensure accurate alignment and register. The photomasked sheet is exposed to a suitable light source, such as an ultraviolet rich light to harden the photoresist in the images of the needle blanks and carrier strips. The photomasks are removed and the unexposed photoresist is removed by subjecting the plate to a suitable developer designed for use with the particular photoresist chosen. The remaining photoresist may be further hardened by baking the sheet at 200–300 degrees Fahrenheit for approximately 10 minutes. The result is a solid metal sheet coated with etchant resistant photoresist in the images of needle blanks 12 and carrier strips 14.

The coated sheet is then subjected to an etch bath, preferably as 36 to 42 degrees Celsius Baumé aqueous ferric chloride, or an aqueous solution of hydrochloric acid and either ferric chloride or nitric acid, where the metal is dissolved from the areas not covered by the etchantresistant, photo-sensitive material 120. The sheet is immersed just long enough so that approximately 50% of the thickness of metal 130 on each side is etched away for approximately minutes. The etch bath chemically etches or removes the areas of the metal sheet not protected by the hardened photoresist. As noted above, the etching process is progressive and etches away laterally on the surface as well as into the face of the exposed metal. Once the fully etched sheet 10 is removed from the etch bath it is rinsed to neutralize any remaining etchant. The etched sheet 10 may then be subjected to a suitable stripper to remove the hardened photoresist and rinsed again.

Figure 4:
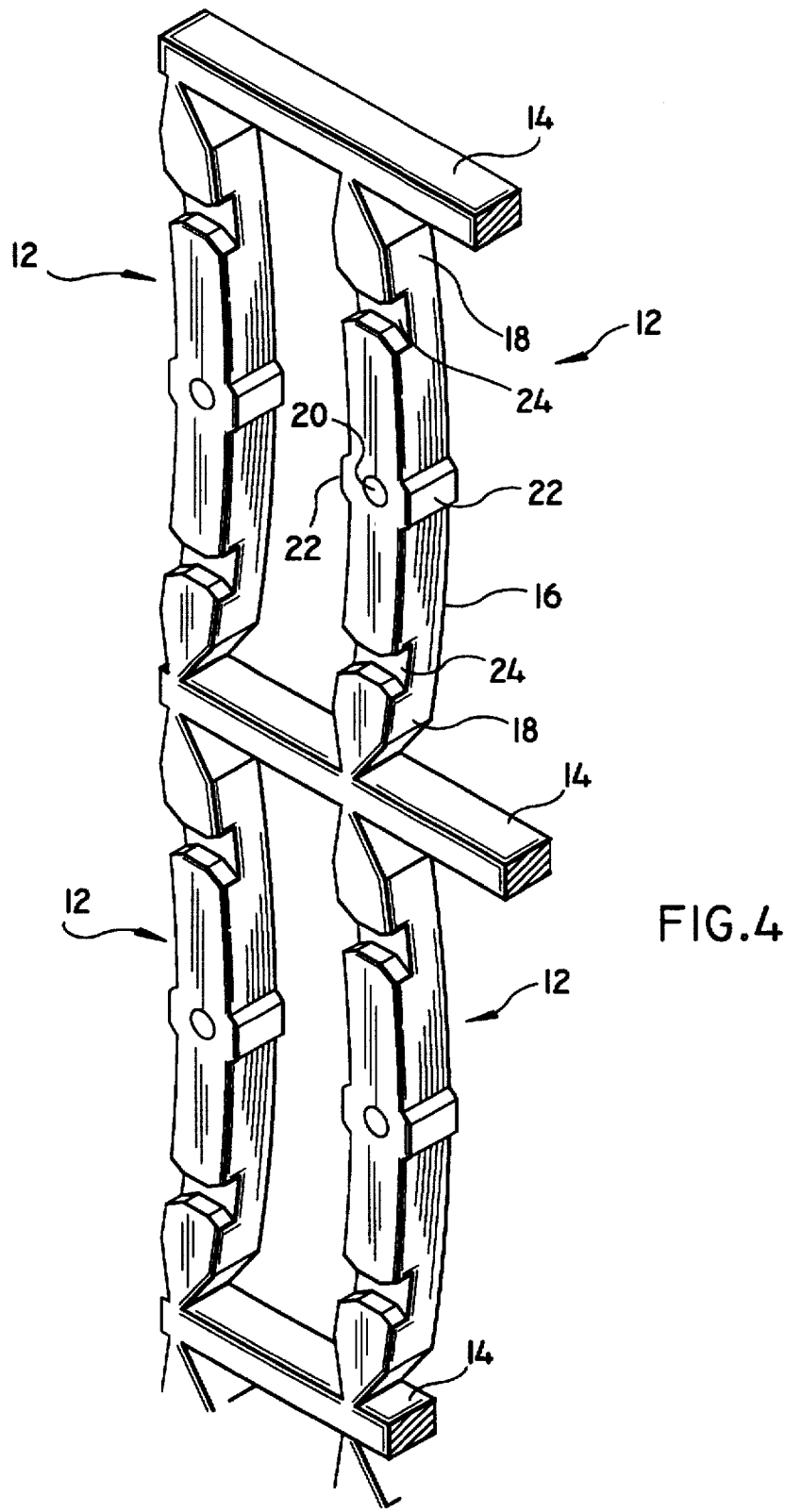
FIG. 4 is an enlarged perspective view of a portion of the sheet of surgical incision member blanks of FIG. 1.

Referring now to FIG. 4, the resultant needle blanks 12 have a generally rectangular or "beam" cross-section which further increases the bend strength of the finished needles. By varying the etch bath composition and duration, the degree of lateral etching to round the edges and shape of the cross-section of the needle blank can be controlled while generally retaining the strength advantages of a beam construction without attendant compressing of the needle stock. Additionally, the depth of the suture hole etched in both sides of the needle blank can be adjusted to etch completely through the needle blank or only as a pilot hole on one or both sides for further mechanical or laser drilling. As shown, needle blank 12 includes body portion 16 connected to carrier strips 14 at each of the pointed end portions 18. Crimping bulges 22 are adjacent suture hole 20 and slots 24 are adjacent each pointed end portion 18. Further, sheet 10 may be subjected to a second diluted etch bath to further refine or "mill" the needle blank shape. The additional etch step may also polish the suture holes and slots.

Prior to removing the needle blanks from the carrier strips the entire sheet 10 may be heat treated to further strengthen the needle blanks. Preferably, sheet 10 is heat treated in the manner disclosed in U.S. Pat. No. 5,411,613. For example, sheet 10 may be heated at about 400° C. to about 500° C. for about 30 minutes to 90 minutes, preferably under vacuum. Additionally, the sheet may be electropolished using known methods to smooth the outer surfaces of the needle blanks.

Needle blanks 12 may be removed from sheet 10 by several methods. In one embodiment, an etchant resistive adhesive backing, such as a vinyl copolymer for example, is affixed to one side of sheet 10 and sheet 10 is subjected to a mild or diluted etching bath to dissolve the connections between needle blanks 12 and carrier strips 14. This additional etching process has the additional advantage of providing the aforementioned "milling" by smoothing the edges of needle blanks 12 as well as refining the overall shape. By etching needle blanks 12 free of carrier strips 14 no additional stresses are introduced into needle blanks 12. With needle blanks 12 individually held on the adhesive backing any number of additional operations, such as hole drilling, suture attachment, etc., may be performed on all the needle blanks quickly and simultaneously.

Alternatively, needle blanks 12 may be separated from carrier strips 14 by conventional methods, such as mechanical or laser cutting or even bending to break the connections. Any minor stresses introduced into pointed tip portions 18 connected to carrier strips 14 by these alternative methods will obviously be localized at pointed tip portions 18 and will not affect the bend strength of needle blanks 12 to any significant extent.

Figure 5:
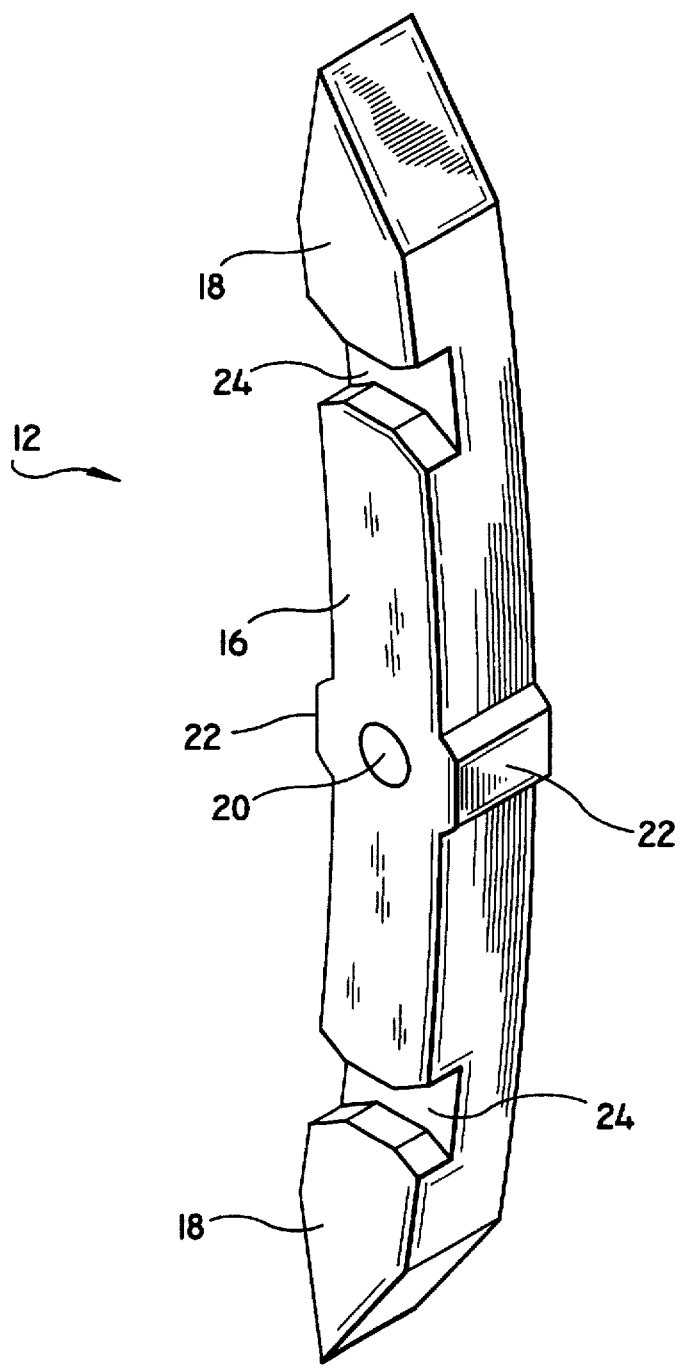
FIG. 5 is an enlarged perspective view of a single surgical incision member blank separated from the sheet of FIG. 4.

Referring now to FIG. 5, there is show a single needle blank 12 after removal from one or more carrier strips 14. As noted above, needle blank 12 has a generally beam shaped configuration which is generally stronger than a pure round cross sectional shape. Needle blank 12 includes body portion 16 having pointed end portions 18 at each end thereof. Needle blank 12 also includes the aforementioned suture hole 20 and crimping bulges 22. Slots 24 are also provided adjacent each pointed end portion 18 and, preferably, on one side only of needle blank 12.

Figure 7:
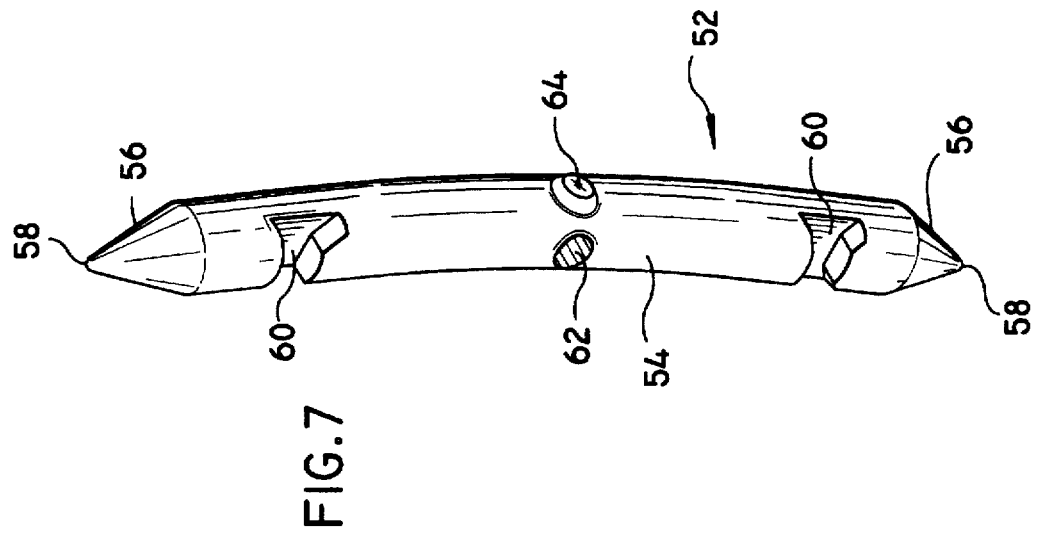
FIG. 7 is a perspective view of the surgical incision member of FIG. 6.
Figure 6:
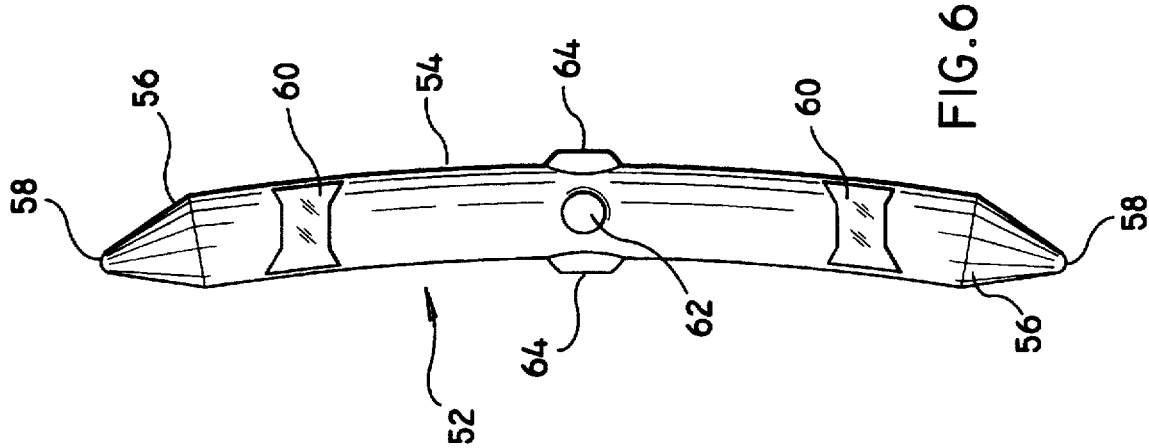
FIG. 6 is side plan view of a surgical incision member after tumbling.

Once needle blanks 12 have been removed from carrier strips 14, they may be further smoothed and refined by tumbling them in a suitable tumbling media for a predetermined time such as disclosed in U.S. Pat. No. 5,447,465. While tumbling is the preferred method of refinement, it is also within the contemplated scope of the disclosure to refine the needle blanks by various other means, such as, for example, by etching. Preferably, the refining process will be performed in such as manner so as to round or blunt the pointed tip portions 18 to form tissue penetrating radiused tip needles as shown in FIGS. 6 and 7. Preferably, the radius imparted to the needle blank tips is approximately 0.005 to 0.015 inches, and more preferably 0.007 inches.

Referring now specifically to FIGS. 6 and 7, the finished surgical incision member 52 has a relatively rounded-off body portion 54 with opposed pointed tip portions 56. As noted above, preferably pointed tip portions 56 have radiussed tissue penetrating tips 58. Slots 60 are defined in body portion 54 and are oriented substantially perpendicular to both a longitudinal axis of body portion 54 and a longitudinal axis of a suture hole 62. Crimping bulges 64 are formed adjacent suture hole 62.

The resultant surgical needles formed by the above described process have been tested for bend strength on bend strength testing apparatus such as that disclosed in U.S. Pat. Nos. 5,022,273 and 5,297,440. The results of the tests are summarized below.

It will be understood that various modifications can be made to the embodiments disclosed herein. For example, the connections between the carrier strips and needle blanks may be located at other non-critical positions along the body portion other than the pointed tip portions. Further, as noted above, various other needle stock materials, photoresists and etchants may be used with similar effect. Additionally, various other complex structural characteristics, such as, channels, for example, may be provided for by etching or by further mechanical processing after removal from the sheet. Therefore, the above description should not be construed as limiting, but merely as exemplification of preferred embodiments. Those skilled in the art will envision other modifications to the disclosure within the scope and spirit of the claims appended hereto.

What is claimed is:

1. A method of producing a surgical needle blank comprising the steps of:

(a) coating opposite sides of a metal sheet with a light sensitive photoresist;

(b) exposing the photoresist with light in the image of a plurality of surgical needle blanks, each needle blank having opposed pointed ends, wherein the light image includes at least one carrier strip and a plurality of surgical needle blanks attached at at least one of their pointed ends in spaced relationship to the strips;

(c) removing unexposed photoresist, to thereby leave in place on the metal sheet hardened photoresist in the image of a plurality of surgical needle blanks attached to the carrier strips; and (d) exposing the product of step c to an etchant to remove metal not protected by the hardened photoresist, to thereby form a plurality of surgical needle blanks having opposed pointed ends and attached at at least one of the pointed ends to a carrier strip.

2. The method according to claim 1, wherein the step of exposing the photoresist with light includes exposing the photoresist with light in the image of a plurality of surgical needle blanks, each needle blank image having an opposed pair of crimping bulges.

3. The method according to claim 1, wherein the step of exposing the photoresist with light includes exposing the photoresist light in the image of a plurality of surgical needle blanks, each needle blank image having a slot adjacent each pointed end.

4. The method according to claim 1, wherein the step of exposing the photoresist with light includes exposing the photoresist with light in the image of a plurality of surgical needle blanks, each needle blank image having a suture hole intermediate the pointed ends.

5. The method according to claim 1, further comprising the step of drilling a suture hole through the surgical needle blanks.

6. The method according to claim 1, further comprising the step of heat treating the surgical needle blanks.

7. The method according to claim 1, further comprising the step of electropolishing the surgical needle blanks.

8. The method according to claim 1, further comprising the step of removing the surgical needle blanks from the strips.

9. The method according to claim 8, further comprising the step of tumbling the surgical needle blanks to form surgical needles.

10. The method according to claim 1, wherein the step of exposing the photoresist includes the step of exposing the opposite sides of the metal sheet to different images.

11. The method according to claim 1, wherein the sheet includes at least two carrier strips and the needle blanks are connected to the carrier strips at both pointed ends.

* * * * *